(12) United States Patent
Zeitouny et al.

(10) Patent No.: US 10,238,283 B2
(45) Date of Patent: Mar. 26, 2019

(54) LENS SYSTEM FOR INSPECTION OF AN EYE

(71) Applicant: Elbit Systems Ltd., Haifa (IL)

(72) Inventors: Abraham Zeitouny, Haifa (IL); Ron Schneider, Haifa (IL)

(73) Assignee: ELBIT SYSTEMS LTD., Haifa (IL)

( * ) Notice: Subject to any disclaimer, the term of this patent is extended or adjusted under 35 U.S.C. 154(b) by 0 days.

(21) Appl. No.: 15/525,268

(22) PCT Filed: Nov. 9, 2015

(86) PCT No.: PCT/IL2015/051076
§ 371 (c)(1),
(2) Date: May 8, 2017

(87) PCT Pub. No.: WO2016/071913
PCT Pub. Date: May 12, 2016

(65) Prior Publication Data
US 2018/0078133 A1    Mar. 22, 2018

(30) Foreign Application Priority Data
Nov. 9, 2014   (IL) .......................................... 235594

(51) Int. Cl.
*A61B 3/12* (2006.01)
*A61B 3/00* (2006.01)
(Continued)

(52) U.S. Cl.
CPC .............. *A61B 3/12* (2013.01); *A61B 3/0008* (2013.01); *A61B 3/102* (2013.01); *A61B 3/125* (2013.01); *A61B 90/36* (2016.02)

(58) Field of Classification Search
CPC ......... A61B 3/12; A61B 3/0008; A61B 3/102; A61B 3/125
See application file for complete search history.

(56) References Cited

U.S. PATENT DOCUMENTS 4,657,357 A    4/1987  Nishimura et al.
6,008,834 A *  12/1999 Lewis .................... G02B 26/10
                                                  347/241
(Continued)

FOREIGN PATENT DOCUMENTS

| CN | 1486677 A     | 4/2004 |
| WO | 95/14254 A1   | 5/1995 |
| WO | 2014/151114 A1 | 9/2014 |

OTHER PUBLICATIONS

International Search Report and Written Opinion for PCT/IL2015/051076, dated Feb. 29, 2016.
(Continued)

*Primary Examiner* — William R Alexander
*Assistant Examiner* — Ephrem Z Mebrahtu
(74) *Attorney, Agent, or Firm* — Merchant & Gould P.C.

(57) ABSTRACT

A novel surgical lens system including a lens and a reflective element. The lens is placed on, or above, a cornea of an eye of a subject for enabling inspection of the eye. The reflective element is incorporated into the lens. The reflective element reflects a light beam toward the eye of the subject. The reflective element increases the divergence of the light beam, such that the divergence of the reflected light beam is larger than the divergence of the light beam. The light beam is emitted by a non-invasive light source positioned externally to the eye.

14 Claims, 2 Drawing Sheets

(51) Int. Cl.
*A61B 3/10* (2006.01)
*A61B 3/125* (2006.01)
*A61B 90/00* (2016.01)

(56) References Cited

U.S. PATENT DOCUMENTS

| | | | |
|---|---|---|---|
| 7,072,104 B2 | 7/2006 | Okamura et al. | |
| 2006/0050229 A1* | 3/2006 | Farberov | A61B 3/117 351/159.02 |
| 2007/0081166 A1* | 4/2007 | Brown | A61B 3/1005 356/479 |
| 2009/0185135 A1 | 7/2009 | Volk | |
| 2012/0050683 A1* | 3/2012 | Yates | A61B 3/1208 351/219 |
| 2016/0000324 A1* | 1/2016 | Rege | A61B 3/0008 351/206 |
| 2016/0161762 A1* | 6/2016 | Heacock | G02B 1/041 351/159.02 |
| 2017/0038834 A1* | 2/2017 | Wilson | G06T 7/215 |

OTHER PUBLICATIONS

Office Action for Chinese Patent Application No. 2015800608378, dated Jun. 28, 2018.
English translation of Chinese Office Action issued in Application No. 2015800608378.

* cited by examiner

LENS SYSTEM FOR INSPECTION OF AN EYE

This application is a National Stage Application of PCT/IL2015/051076, filed Nov. 9, 2015, which claims benefit of Israeli Patent Application No. 235594, filed Nov. 9, 2014, which applications are incorporated herein by reference. To the extent appropriate, a claim of priority is made to each of the above disclosed applications.

FIELD OF THE DISCLOSED TECHNIQUE

The disclosed technique relates to a lens for the surgical field, in general, and to methods and systems for observing a retina of an eye by employing a retinal-surgery lens incorporating a mirror arranged to reflect light onto the retina, in particular.

BACKGROUND OF THE DISCLOSED TECHNIQUE

In the human vision system, the retina is a light-sensitive layer of tissue, covering the inner surface of the eye. An image of a viewed scene is created on the retina (i.e., through the eye lens). Light impinging on the retina triggers nerve impulses sent to visual areas of the brain.

Retinal surgeries, as known in the art, involve the placement of a macular lens on the eye and insertion of an illumination optical fiber into the eye ball for illuminating the retina. For example, one surgeon (or a fixture) holds the macular lens on the top surface of the eye, the cornea, while another holds the illumination fiber and other surgical tools. Thus, the illumination fibers are aimed manually. Additionally, the distribution angle of the illuminating fiber beam (i.e., or the illuminated spot generated thereby) is relatively narrow. Therefore, the surgeon holding the fiber has to constantly redirect the illumination fiber for illuminating the area of interest investigated under a microscope.

Reference is now made to US Patent Application Publication No. 2012/0050683 to Yates, entitled "Self-Illuminated Handheld Lens for Retinal Examination and Photography and Related Method thereof". This publication is directed to a handheld fundus lens with integrated lighting fibers. The hand held fundus lens of this publication provides illumination to the patient's retina from a point source of light through fiber optics strands. The light source is positioned outside the lens and is directly coupled to the fiber optic strands. A light channel is ground into the contact lens, and the fiber optic strands are inserted into this light channel. The fiber optic strands are formed into an illumination ring abutting the contact lens.

WO 95/14254 to Donald A. Volk entitled "Indirect ophthalmoscopy lens system and adapter lenses" is directed to an ophthalmoscopic or gonioscopic lens system. The indirect ophthalmoscopy lens comprises a hand-held, pre-set or fixed system having at least two lens elements each having first and second surfaces. The at least two lens elements are positioned adjacent one another in a housing, such that the refractive properties of each are combined to converge light from an illumination light source to the entrance pupil of the patient's eye to illuminate the fundus thereof and form a fundus image to be viewed. The adapter lens systems of this invention are designed for use with an associated ophthalmoscopic lens, enabling selective modification of the optical characteristics of the ophthalmoscopic lens system in a predetermined manner.

US 2009/0185135 to Donald A. Volk entitled "Real image forming eye examination lens utilizing two reflective surfaces providing upright image" describes a diagnostic and therapeutic contact lens for use with biomicroscopes for the examination and treatment of structures of the eye. The lens comprises a contacting surface adapted for placement on the cornea of an eye, two reflecting surfaces, and a refracting surface. A light ray emanating from the structure of the eye enters the lens and contributes to the formation of a correctly oriented real image. The light ray is reflected in an ordered sequence of reflections, first as a negative reflection in a posterior direction from an anterior reflecting surface and next as a positive reflection in an anterior direction from a posterior reflecting surface. The light ray contributes to forming the image of the structure of the eye either anterior to the lens or within the lens and proceeds along a pathway to the objective lens of the biomicroscope used for stereoscopic viewing and image scanning.

SUMMARY OF THE PRESENT DISCLOSED TECHNIQUE

It is an object of the disclosed technique to provide a novel surgical lens system including a lens and a reflective element. The lens is placed on, or above, a cornea of an eye of a subject for enabling inspection of the eye. The reflective element is incorporated into the lens. The reflective element reflects a light beam toward the eye of the subject. The reflective element increases the divergence of the light beam, such that the divergence of the reflected light beam is larger than the divergence of the light beam. The light beam is emitted by a non-invasive light source positioned externally to the eye.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by providing a macular lens incorporating a mirror and a light guide. The light guide directs an illumination light beam from a light source to the mirror. The mirror reflects the light beam toward the eye of a subject to illuminate the eye (e.g., to illuminate the retina of the subject for inspection). Additionally, the mirror may have optical power and be configured to increase the divergence of the reflected light beam. In accordance with an embodiment of the disclosed technique, the reflected light beam passes through the macular lens, which further increases the divergence of the reflected light beam. In other words, the mirror (and possibly also the macular lens) increases the diameter of the illumination light beam on the retina of the subject.

In accordance with another embodiment of the disclosed technique the macular lens (including the incorporated mirror) is disposable. In this manner, a physician can inspect the eye of a subject via such a disposable macular lens and dispose of the macular lens afterwards, employing another such macular for inspecting another subject.

The term "beam diameter" as referred to herein below relates to the diameter of the cross section of a light beam on a plane perpendicular to the beam axis. That is, the beam diameter is the diameter of the spot the beam lights on a plane perpendicular to the beam axis. The term "beam divergence" as referred to herein below relates to the increase in beam diameter with distance (i.e., the beam angular distribution). The term "inspection" as referred to herein with respect to inspection of the eye of a subject, relates to inspection of the eye or of different portions of the eye for various purposes. For example, the inspection can relate to observation by a physician for medical diagnostic, for retinal surgery or for imaging in general. The inspection can further relate to other purposes, such retinal scan for biometric identification, and any other purpose which requires inspecting the eye or various portions thereof.

Figure 1:
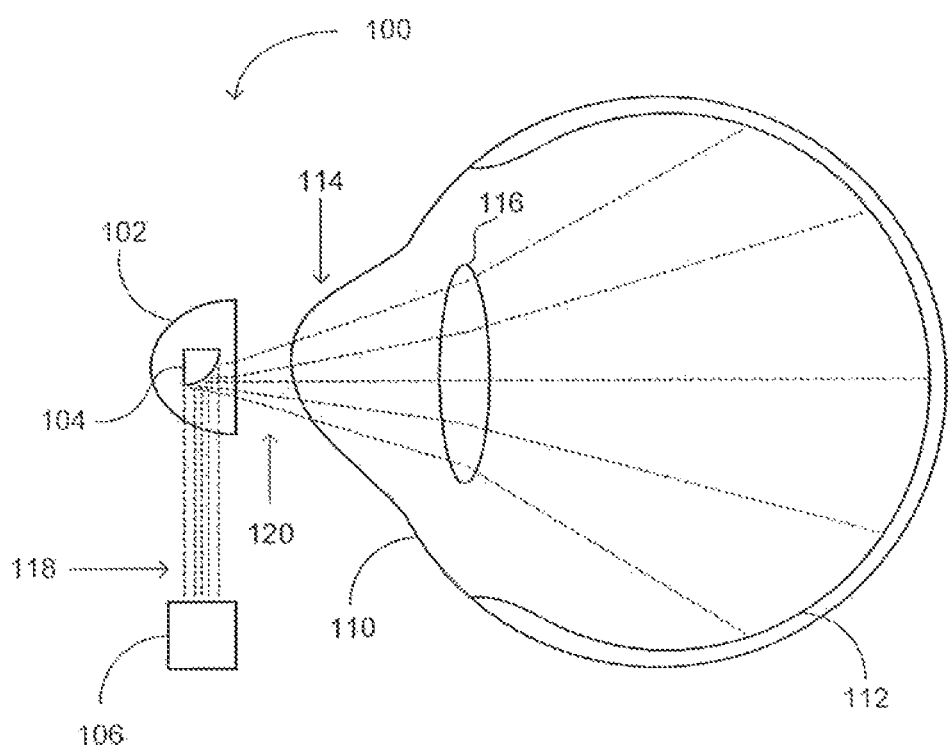
FIG. 1 is a schematic illustration of a surgical lens system, constructed and operative in accordance with an embodiment of the disclosed technique.

Reference is now made to FIG. 1, which is a schematic illustration of a surgical lens system, generally referenced 100, constructed and operative in accordance with an embodiment of the disclosed technique. Lens system 100 includes a surgical lens 102, a mirror 104 and a light source 106. In general, light source 106 is positioned outside the field of view (FOV) of the lens. In the embodiment shown in FIG. 1 light source 106 is positioned perpendicular to the FOV of lens 102. In other embodiments, light source 106 can be positioned also substantially perpendicular to the FOV of the lens (i.e. in a range of −/+10 degrees). Mirror 104 is incorporated into lens 102, for example, at the center of surgical lens 102 (i.e., the center on a plane perpendicular to the optical axis of surgical lens 102). The position of mirror 104 relative to the center of surgical lens 102 can affect the illumination characteristics (characteristics like illumination uniformity, stray lights reflected to the optical system or camera, illumination field of view coverage etc.) In general, mirror 104 can be placed at different positions relative to lens 102 as long as it is located at the central region of lens 102 away from the periphery thereof. Light source 106 is optically coupled with mirror 104. Lens system 100 may further include a waveguide (not shown) optically coupled between light source 106 and mirror 104.

As used in this disclosure the term 'optically coupled' describes an aspect of the optical relations between light source 106 and mirror 104. Light emitted from light source 106 is conveyed to mirror 104 by using different techniques. As an example, an exit aperture located in light source 106 is placed near a specific location on the lens (an entrance aperture). A mechanical fixture can be used in order to correctly position the exit aperture near the entrance aperture. The light then exits the light source exit aperture and enters directly into the lens through the entrance aperture. Subsequently to entering the lens, the light travels through a waveguide that directs the light to the mirror. The waveguide is optionally selected from a recess, a depression, a change in the lens index of refraction or an implantation of different material in the lens, etc. The light source aperture size, the divergence angle, the entrance aperture in the lens and waveguide can be designed according to the user's requirements. In a further embodiment of the disclosed technique, a small light fiber is tunneled through the lens to reach a point located a short distance from the mirror and thus illuminate the mirror directly. In an additional embodiment of the disclosed technique, the light can be illuminated directly towards the mirror (with no waveguide), using a laser source (or other) with a very narrow angle of divergence.

Surgical lens 102 is attached to an eye 110 of a subject and in particular is placed on a cornea 114 of eye 110 similarly to a contact lens, or at a short distance from the cornea. Therefore, lens 102 can be of various sizes to fit various subjects. For example, for inspecting the eye of a child, a user would use a smaller lens than for an adult. The eyes of different users can vary by size, cornea convexity, and the like. Surgical lens 102 is also referred to herein below as macular lens 102 or simply lens 102.

Lens 102 is employed for inspection of eye 110 or of portions thereof, such as the retina, the eye lens, and the like. The inspection can be performed by employing the macular lens alone or employing the macular lens as a component of an inspection system including additional components. For example, lens 102 is employed for retinal diagnostic and surgical operations, and enables a surgical microscope (e.g., ophthalmic microscope) to image a retina 112 via cornea 114 and eye lens 116. When inspecting the subject's retina via a microscope, one should add a relay component to the microscope for adapting the microscope to compensate for light divergence by the eye lens of subject. The macular lens of the disclosed technique serves as such relay component. For example, macular lens 102 is an aspheric fundus lens.

Lens 102 can be of varying optical power, as required by the inspection task at hand. For example, a lens for inspecting the retina might differ from a lens for inspective the eye lens of the subject. The differences can relate to the focal distance, the optical power, the field of view (FOV), and other optical and physical parameters of the lens.

Mirror 104 is a reflective element, also referred to herein below as reflective element 104. Mirror 104 may be partially reflective as a function of power or wavelength (e.g., reflecting only a selected waveband). Mirror 104 is configured to reflect (i.e., redirect) light received from light source 106 toward eye 110. That is, mirror 104 is constructed, positioned and coupled with the other components of surgical lens system 100 in such a way that it reflects the light produced by light source 106 toward eye 110.

Mirror 104 may further be configured to increase the divergence of the light reflected thereby. The divergence increase of mirror 104 is adapted to the inspection task at hand. For example, the user can use a different lens system having a different mirror (differing by its beam divergence increase) for different inspection tasks. Generally, mirror 104 increases the divergence of the light beam, such that the FOV of lens 102 would be illuminated. It is noted that the divergence of the light beam may further be increased by lens 102 and by the eye lens, which should be considered when configuring the divergence increase of mirror 104.

Mirror 104 can be composed of several elements. For example, mirror 104 can include several reflecting surfaces, each with different optical power (or with no optical power). Mirror 104 can include a flat mirror (i.e., a reflecting component) and a lens (i.e., a divergence increasing component) coupled therewith. Alternatively, reflective element 104 can be replaced by other optical elements for changing the direction of light, such as a prism, a diffraction grating, or a beam splitter. Generally speaking, the reflective element should redirect the illumination beam toward the eye of the subject. Additionally, the reflective element may be configured to increase the beam divergence of the illumination beam as detailed above.

As mentioned above the mirror (i.e., the reflective element) can be coupled with other optical elements. The optical elements are employed for augmenting the function of the mirror (e.g., flat mirror coupled with a lens), or for complementing it (e.g., both the mirror and the lens increase the beam divergence). The optical element coupled with the mirror can serve other functions as well, such as improving the light uniformity.

The beam divergence angle of the reflected light covers the field of view (FOV) of macular lens 102. In this manner, an inspected area, inspected via lens 102, is illuminated. Moreover, the reflected light illuminates the FOV of macular lens 102 in a uniform manner. It is noted that, non-uniform illumination may affect images of the retina and may lead to erroneous diagnostics.

Mirror 104 can be incorporated into lens 102, located within a niche within lens 102 or coupled with lens 102 on either side of lens 102. In case mirror 104 is located within lens 102 or coupled to the side of lens 102 further from the eye, the light reflected by the mirror passes through at least a portion of lens 102. In this case, lens 102 increases the divergence of the reflected light beam, thereby augmenting the beam divergence increase of mirror 104. Additionally, mirror 104 is configured such that eye lens 116 further increases the divergence of the reflected light beam. It is noted that mirror 104 partially occludes the FOV of lens system 100. Therefore, mirror 104 should be small enough such that the occlusion would not adversely affect the inspection of the eye. For example, mirror 104 can have a diameter ranging between 1-3 millimeters. Mirror 104 can be positioned at different heights along the optical axis. The occlusion severity and type is a function of the mirror height. According to the disclosed technique, the occlusion of a mirror positioned outside of the focal plane, will cause certain effects like decreasing the illumination level, the sharpness of the image etc. but will not cause complete obstruction of portions of the perceived image. Contrary to the disclosed technique, the occlusion of a mirror positioned in the focal plane, will cause obstruction of the perceived image.

In accordance with an embodiment of the disclosed technique, mirror 104 is positioned at the center of lens 102 along the optical axis of lens 102. In such a case, the reflected light beam and the FOV of macular lens 102 are coaxial. Put another way, reflected light beam 120 provides zero-angle illumination. In accordance with another embodiment mirror 104 is positioned off-axis. For example, mirror 104 is positioned off the axis of macular lens 102 but is still located in the central region of macular lens 102 away from the periphery of lens 102.

In accordance with another embodiment of the disclosed technique, mirror 104 can have various optical properties, for affecting the reflected light beam. For example, mirror 104 can affect the polarity, the wavelength (e.g., by blocking a selected waveband), or other properties of the light beam. Mirror 104 can be coated with various coatings for inducing these optical properties.

In accordance with yet another embodiment of the disclosed technique, mirror 104 can be coupled to lens 102 via a mounting mechanism which allows mirror 104 to be moved. Thereby, mirror 104 can be employed as a scanning mirror for illuminating different areas of the eye of the subject.

Light source 106, including an output port of light source 106 (not referenced), is positioned externally to the eye. In other words, light source 106 is a noninvasive light source. Light source 106 is configured to generate illumination light beam 118. Light source projects light beam 118 toward mirror 104 (or toward a waveguide of surgical lens system 100 leading to mirror 104 and incorporated into macular lens 102). In accordance with an embodiment of the disclosed technique, light source 106 produces a narrow light beam 118, which is thereafter diverged by mirror 104, macular lens 102 and eye lens 106 to illuminate the FOV of macular lens 102.

Light source 106 can produce illumination light at any desired light wavelength, or other illumination characteristics (e.g., wavelength, polarization, intensity and the like), as required by the user and the task at hand. Additionally, the illumination beam can be modulated. The light source can produce light pulses instead of a continuous beam. The illumination can be synchronized with, or otherwise controlled, by an external device, such as an imaging device. Generally, the light source produces the illumination required to the task at hand, and the mirror directs the illumination beam (or pulse) toward the inspected area.

It is noted that the light source can be coupled with the lens system of the disclosed technique via intermediate elements such as a fiber and a connector. For example, the light source can be a Light Emitting Diode (LED) mechanically (or opto-mechanically) connected to the lens.

During operation, a user (e.g., an ophthalmologist) places macular lens 102 on cornea 114 and turns on light source 106. Light source 106 directs light beam 118 toward reflective element 104. Reflective element 104 reflects light beam 118 toward eye 110. In other words, reflective element directs a reflected light beam 120 toward eye 110. The user inspects eye 110 (illuminated by reflected light beam 120) via macular lens 102.

As can be seen in FIG. 1, reflective element 104 increases the divergence of reflected light beam 120. That is, the divergence of reflected light beam 120 is larger than that of light beam 118. As can further be seen in FIG. 1, each of macular lens 102 and eye lens 116 further increases the divergence of reflected light beam 120. It is noted that the divergence angle of reflected light beam 120 covers the FOV of macular lens 102, such that the inspected portion of retina 112 is illuminated. Additionally, reflected light beam 120 illuminates the inspected portion of retina 112 in a uniform manner.

In accordance with an embodiment of the disclosed technique, the user can hold the lens via a holder (not shown). The light source can be incorporated into (or connected to) the holder. Alternatively, the lens can be held in place by a mechanical fixture (not shown). The light source can be incorporated into (or connected to) the mechanical fixture.

In accordance with another embodiment of the disclosed technique, macular lens 102 (including incorporated mirror 104 and the optional incorporated waveguide) is disposable. In this manner, the user places lens 102 over cornea 114 of the subject, and couples it to light source 106. The user inspects eye 110 via lens 102, and thereafter disposes of lens 102. The user employs a new disposable lens 102 for the next subject. Light source 106 can be reused. As the lens system is disposable and is employed for a single subject, different lens systems can be of different sizes for adapting to various users. Additionally, the reflective elements can be of various optical properties, such as various degrees of divergence increase, for different inspection tasks. In accordance with an alternative embodiment, the macular lens can be reused (after being sanitized) for a plurality of subjects. Further alternatively, some elements of the macular lens system are reusable and some are disposable. For example the light source and the lens holder are reusable, while the lens and the incorporated mirror and waveguide, are disposable.

In accordance with yet another embodiment of the disclosed technique, the lens system includes a zooming mechanism for controlling the zoom of the light beam. For example, the mirror is coupled with lenses which serve as a zoom mechanism for the illumination light beam. Alternatively, the light source can be moved with respect to the mirror for varying the zoom of the illumination beam.

In accordance with yet another embodiment of the disclosed technique, system 100 is employed for inspection of other body cavities which require illumination, such as the ears of the subject. System 100 is placed over the body cavity, the mirror reflects the illumination beam toward the cavity, and the user inspects the illuminated cavity via the lens.

Figure 2:
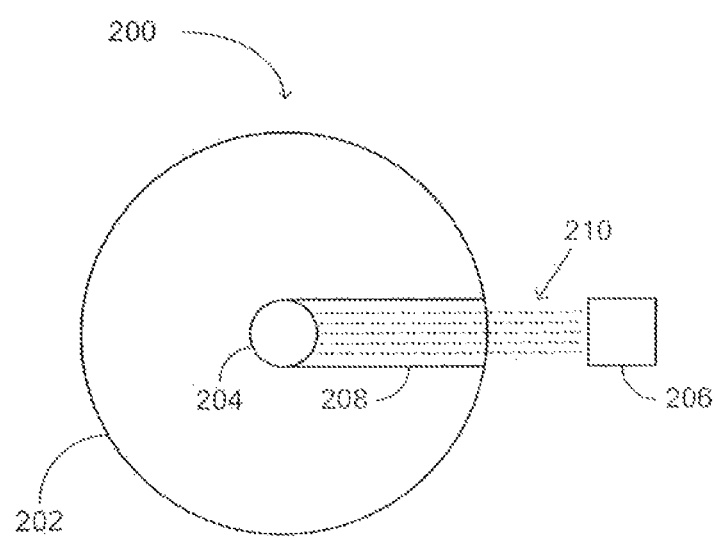
FIG. 2 is a schematic illustration of a surgical lens system, constructed and operative in accordance with another embodiment of the disclosed technique.

Reference is now made to FIG. 2, which is a schematic illustration of a surgical lens system, generally referenced 200, constructed and operative in accordance with another embodiment of the disclosed technique. FIG. 2, depicts a cross section of surgical lens system 200 along a plane perpendicular to the optical axis of the lens. Lens system 200 includes a lens 202, a mirror 204, a light source 206 and a waveguide 208 (or a light guide 210). Mirror 204 and waveguide 208 are incorporated into lens 202. Mirror 204 is optically coupled with light source 206 via waveguide 208. That is, a light beam 210 irradiated by light source 206 enters waveguide 208 and is directed thereby toward mirror 204. Each of lens 202, mirror 204 and light source 206 is substantially similar to lens 102, mirror 104, and light source 106, of FIG. 1, respectively. Waveguide 208 (also referred to herein as light guide 208) is an optical element for directing light from one end of waveguide 208 (coupled with light source 206) to the opposite end of waveguide 208 (coupled with mirror 204). For example, waveguide 208 can be an optical fiber, a dedicated structure within lens 102, a series of mirrors or other optical elements that can guide light, and the like.

A user holds (or places) lens 102 over a cornea of an eye of a subject. Light source 206 irradiates illumination beam 210 into waveguide 208. Waveguide 208 guides illumination beam 210 toward mirror 204. Mirror 204 reflects illumination beam 210 toward the eye of the subject, illuminating the eye for inspection via lens 202. As can be seen in FIG. 2, mirror 204 is positioned at the center of lens 202 (i.e., along the optical axis of lens 202). Thereby, the reflected light beam and the FOV of lens 202 are coaxial (i.e., zero-angle illumination). Alternatively, mirror 204 can be located off-axis.

Figure 3:
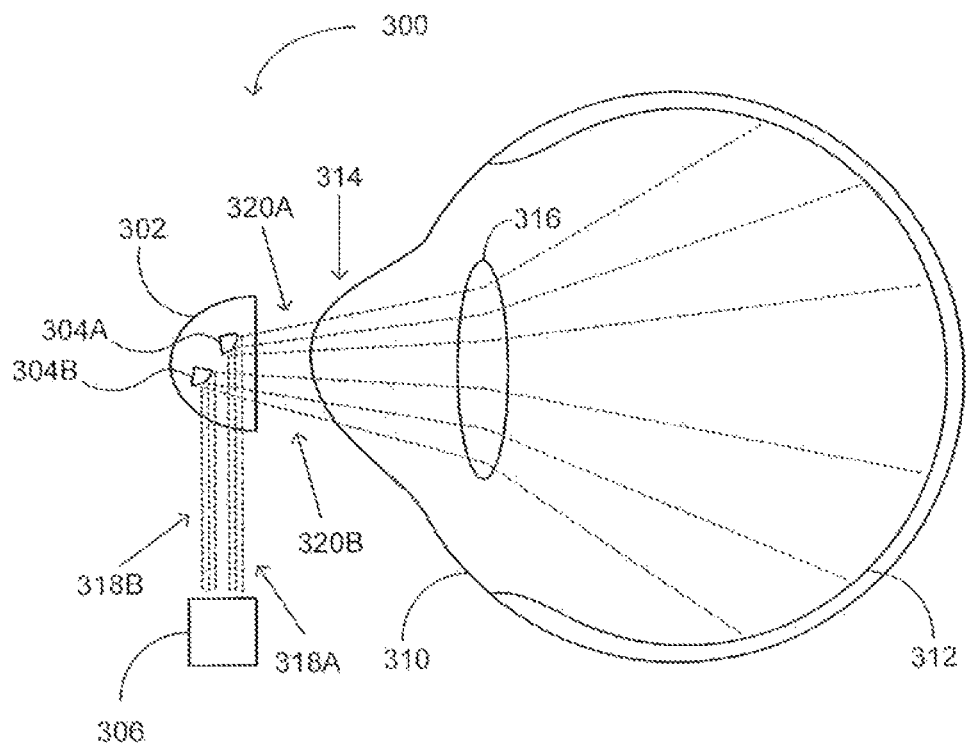
FIG. 3 is a schematic illustration of a surgical lens system, constructed and operative in accordance with a further embodiment of the disclosed technique.

Reference is now made to FIG. 3, which is a schematic illustration of a surgical lens system, generally referenced 300, constructed and operative in accordance with a further embodiment of the disclosed technique. Lens system 300 includes a surgical lens 302, a first mirror 304A, a second mirror 304B, and a light source 306. Mirrors 304A and 304B are incorporated into lens 302. Light source 306 is optically coupled with mirror 304. Lens system 300 can further include a waveguide (not shown) coupled between light source 306 and each of mirrors 304A and 304B for guiding light irradiated by light source 306 toward mirrors 304A and 304B.

Light source produces a light beam composed of a first light beam portion 318A and a second light beam portion 318B (light beams 318A and 318B). First light beam portion 318A impinges on the reflective surface of mirror 304A and is reflected thereby as first reflected light beam 320A. Second light beam portion 318B impinges on the reflective surface of mirror 304B and is reflected thereby as second reflected light beam 320B. Each of mirrors 304A and 304B also increases the divergence of the respective reflected light beam. That is, mirror 304A increases the divergence of reflected light beam 320A, and mirror 304B increases the divergence of reflected light beam 320B. Each of lens 302 and eye lens 316 further increases the divergence of reflected light beams 320A and 320B. Reflected light beams 320A and 320B illuminate the FOV of lens 302, thereby allowing inspection of eye 310 via lens 302.

In the example set forth in FIG. 3, there are two mirrors. Alternatively, there could be any number of mirrors each reflecting a portion of the illumination beam irradiated by the light source toward the eye. Each of the mirrors increases the divergence of the beam portion it reflects.

Figure 4:
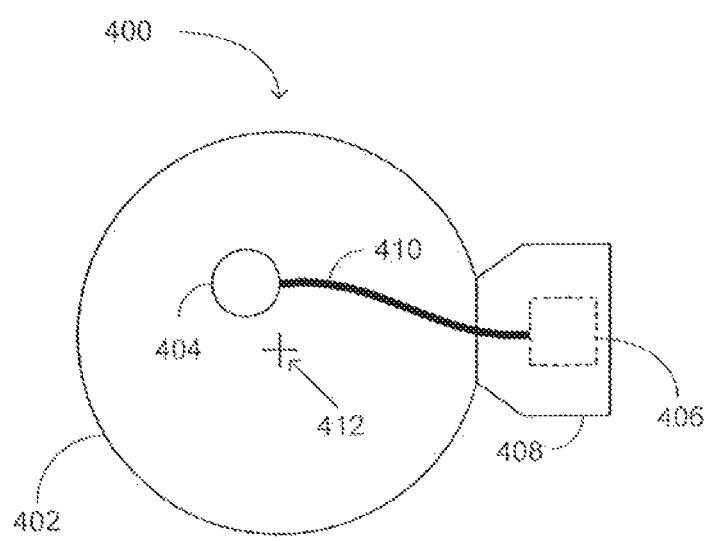
FIG. 4 is a schematic illustration of a surgical lens system, constructed and operative in accordance with another embodiment of the disclosed technique.

Reference is now made to FIG. 4, which is a schematic illustration of a surgical lens system, generally referenced 400, constructed and operative in accordance with yet another embodiment of the disclosed technique. FIG. 4, depicts a cross section of surgical lens system 400 along a plane perpendicular to the optical axis of the lens. Lens system 400 includes a lens 402, a mirror 404, a light source 406, a holder 408 and a fiber 410. Holder 408 is mechanically connected to lens 402. Mirror 404 and fiber 410 are incorporated into lens 402. Light source 406 is incorporated into holder 408. Mirror 404 is optically coupled with light source 406 via fiber 410. Each of lens 402, mirror 404 and light source 406 is substantially similar to lens 102, mirror 104, and light source 106, of FIG. 1, respectively.

Holder 408 is employed for holding lens system 400. That is, a user holds lens system 400 via holder 408 and positions lens 402 over the eye of a patient. Light source 406 is incorporated into holder 408 for reducing the size of lens system 400. Additionally, by incorporating the light source into the holder, the light source is maintained mechanically connected to the lens, and thereby maintained optically aligned with the lens. In case lens 402 is a disposable lens, holder 408 (and incorporated light source 406) are either disposable as well, or are reused and coupled with a new lens for each subject. As opposed to the embodiments shown in FIGS. 1 through 3, light source 406 which is mechanically connected to the lens, can be positioned in any desired direction and is not limited to being positioned perpendicular to the FOV of the lens.

As can be seen in FIG. 4, mirror 404 is positioned off-axis (i.e., away from a center 412 of lens 402). It is noted though, that mirror 404 is located at the central region of lens 402 away from the periphery thereof.

In the examples set forth herein above the mirror incorporating lens of the disclosed technique was exemplified as a retinal surgical lens. However, the lens of the disclosed technique can be adapted to, and employed for, every scenario at which inspection of a darkened area (i.e., requiring illumination) is required, such as other body cavities as, for example, an ear of a subject. In particular, where zero-angle illumination is required, such as for dilated fundus examination or for Optical Coherence Tomography (OCT) applications.

It is noted that the retinal vision mechanism is common among vertebrates. Thus, the lens system of the disclosed technique can also be employed for retinal surgeries of non-human subjects, such as other mammals (e.g., horses or apes), or non-mammals vertebrates (e.g., reptiles or birds).

It will be appreciated by persons skilled in the art that the disclosed technique is not limited to what has been particularly shown and described hereinabove. Rather the scope of the disclosed technique is defined only by the claims, which follow.

The invention claimed is:

1. A lens system for inspection of an eye of a subject comprising:
   a lens arranged to be placed either one of on and above a cornea of said eye; said lens configured to form an image of said eye; and
   a reflective element placed away from the periphery of said lens, so that said reflective element partially occludes a field of view (FOV) of said lens, said reflective element is incorporated into said lens;
   wherein said reflective element being configured to reflect a light beam, emitted by a non-invasive light source positioned externally to said eye, and thereby to direct a reflected light beam toward said eye of said subject, said reflective element being further configured to increase the divergence of said light beam, such that the divergence of said reflected light beam is larger than the divergence of said light beam.

2. The lens system of claim 1, wherein said reflected light beam passes through said lens, and wherein said lens has optical power and is configured to increase the divergence of said reflected light beam, wherein the beam divergence increase of said reflective element is augmented.

3. The lens system of claim 1, wherein a beam diameter of said reflected light beam covers a field of view of said lens on a retina of said eye.

4. The lens system of claim 1, wherein said reflective element is positioned along an optical axis of said lens.

5. The lens system of claim 1, further comprising a waveguide incorporated into said lens, said waveguide arranged to receive said light beam from said light source and to guide said light beam via said lens toward said reflective element.

6. The lens system of claim 5, wherein said waveguide being an optical fiber.

7. The lens system of claim 1, wherein said reflective element includes a plurality of reflective elements positioned such that each of said reflective elements occlude a portion of FOV of said lens, each of said reflective elements being configured to reflect a portion of said light beam.

8. The lens system of claim 1, further comprising a holder by which a user can hold said lens system.

9. The lens system of claim 8, wherein said light source is incorporated into said holder.

10. The lens system of claim 1, wherein said reflective element is not incorporated into said lens, and wherein said reflective element is located within a field of view of said lens.

11. The lens system of claim 1, wherein said reflective element is not incorporated into said lens, and wherein said lens is located within said reflected light beam.

12. The lens system of claim 1, wherein said reflective element is composed of a reflective component and a divergence increase component having optical power.

13. The lens system of claim 1, further comprising a zooming mechanism for controlling the zoom of said light beam.

14. The lens system of claim 1, wherein said lens being a disposable lens by being configured to be coupled with and to be decoupled from said light source.

* * * * *